US008962689B2

(12) United States Patent
Mingrone et al.

(10) Patent No.: US 8,962,689 B2
(45) Date of Patent: Feb. 24, 2015

(54) MEDIUM CHAIN DICARBOXYLIC ACIDS, THEIR DERIVATES AND METABOLIC DISORDERS

(75) Inventors: Geltrude Mingrone, Rome (IT); Catherine Mace, Lausanne (CH)

(73) Assignee: Nestec S.A., Vevey (CH)

( * ) Notice: Subject to any disclaimer, the term of this patent is extended or adjusted under 35 U.S.C. 154(b) by 60 days.

(21) Appl. No.: 12/921,404

(22) PCT Filed: Mar. 9, 2009

(86) PCT No.: PCT/EP2009/052721
§ 371 (c)(1),
(2), (4) Date: Sep. 8, 2010

(87) PCT Pub. No.: WO2009/112455
PCT Pub. Date: Sep. 17, 2009

(65) Prior Publication Data
US 2011/0002900 A1 Jan. 6, 2011

(30) Foreign Application Priority Data
Mar. 10, 2008 (EP) .................... 08152549

(51) Int. Cl.
*A61K 31/194* (2006.01)
*A23L 1/29* (2006.01)
*A23L 1/30* (2006.01)
(52) U.S. Cl.
CPC *A23L 1/30* (2013.01); *A23L 1/3008* (2013.01)
USPC .... 514/574; 424/93.4; 424/93.44; 424/93.45; 424/93.48; 424/93.51
(58) Field of Classification Search
CPC ...... A61K 31/194; A61K 35/741; A23L 1/29; A23L 1/296; A23L 1/30
USPC ............ 424/93.4, 93.44, 93.45, 93.48, 93.51; 514/574
See application file for complete search history.

(56) References Cited

U.S. PATENT DOCUMENTS

| 2,982,658 | A | * | 5/1961 | Betts et al. ................. 427/398.1 |
| 3,360,375 | A | * | 12/1967 | Buddemeyer et al. .......... 426/24 |
| 5,219,604 | A | * | 6/1993 | Klemann et al. .............. 426/531 |
| 5,272,177 | A | | 12/1993 | Mingrone |
| 6,432,448 | B1 | * | 8/2002 | Augello et al. ................ 424/479 |
| 7,311,932 | B1 | * | 12/2007 | Berggren et al. ............... 426/61 |
| 7,618,951 | B2 | | 11/2009 | Monsan et al. |
| 2005/0266069 | A1 | * | 12/2005 | Simmons et al. ............. 424/451 |

FOREIGN PATENT DOCUMENTS

| EP | 1282687 | | 2/2003 |
| EP | 1424074 | | 6/2004 |
| EP | 2100604 | A1 | 9/2009 |
| JP | 61130205 | A * | 6/1986 |
| JP | 61171417 | | 8/1986 |
| JP | 10327805 | A | 12/1998 |
| JP | 2008519831 | A | 6/2008 |
| WO | 2006/052134 | A2 | 5/2006 |

OTHER PUBLICATIONS

Favuzzi "Pharmacokinetics of sebacic acid in rats" European review for medical and pharmacological science, May-Jun. 1999, 3(3), 119-125, Abstract provided.*
Boost Plus, published on: tchomemedical.com/IBS/SimpleCat/Product/asp/product-id/23097698.html, web capture from Jan. 3, 2007 provided courtesy of WaybackMachine.*
Salinari Serenella et al.; "Dodecanedioic acid overcomes metabolic infelxibility in type 2 diabetic subjects," Nov. 2006, American Journal of Physiology, Endocrinology and Metabolism Nov. 2006, vol. 291, NR. 5, pp. E105-E1058, XP002493030 ISSN: 0193-1849 abstract p. E1052, col. 1, paragraph 4, p. E1056, col. 1, paragraph 3.
Greco A V et al. "The metabolic effect of didecanedioic acid infusion in non-insulin-dependent diabetic patients," Nutrition (Burbank, Los Angeles County, Calif.) Apr. 1998, pp. 351-357, XP002493029 ISSN: 0899-9007, abstract, p. 357, col. 2, paragraph 2.
Bonora, et al., "Prevalence of Insulin Resistance in Metabolic Disorders," Diabetes, vol. 47, Oct. 1998, pp. 1643-1649.
Lebovitz, "Insulin resistance: definition and consequences," Exp Clin Endocrinol Diabetes, 109 (2001), Suppl 2:S135-S148.
Raguso, et al., "Dicarboxylic Acids and Glucose Utilization in Humans: Effect of Sebacate," Journal of Parenteral and Enteral Nutrition, p. 9-13, vol. 18, No. 1, 1994.
Warram, et al., "Slow Glucose Removal Rate and Hyperinsulinemia Precede the Development of Type II Diabetes in the Offspring of Diabetic Parents," Annals of Internal Medicine. (1990) 113: 909-915.
European Office Action for European Application No. 08152549.5 mailed Jan. 17, 2011.
Gastaldelli et al., "Influence of Obesity and Type 2 Diabetes on Gluconeogenesis and Glucose Output in Humans", Diabetes, Aug. 2000, vol. 49, pp. 1367-1373.
Salminen et al., "Probiotics: how should they be defined?", Food Science & Technology, 1999, vol. 10, pp. 107-110.
International Search Report and Written Opinion issued Jun. 9, 2009 for related Intl. Appln. PCT/EP2009/052721.
J. Han, et al., "Medium-Chain Oil Reduces Fat Mass and Down-regulates Expression of Adipogenic Genes in Rats," Obesity Research, vol. 11, No. 6, Jun. 2003, pp. 734-744.

* cited by examiner

*Primary Examiner* — Jon P Weber
*Assistant Examiner* — Charles Zoltan Constantine
(74) *Attorney, Agent, or Firm* — K&L Gates LLP

(57) ABSTRACT

The present invention relates in general to medium chain dicarboxylic acids, their derivatives and their uses. In particular, the present invention relates to a composition comprising medium chain dicarboxylic acids and to the use of medium chain dicarboxylic acids and their derivatives for the preparation of products to treat or prevent metabolic disorders. The composition of the present invention can particularly well be used to treat or prevent hyperglycemia, for example diabetes.

11 Claims, 3 Drawing Sheets

MEDIUM CHAIN DICARBOXYLIC ACIDS, THEIR DERIVATES AND METABOLIC DISORDERS

Figure 1:
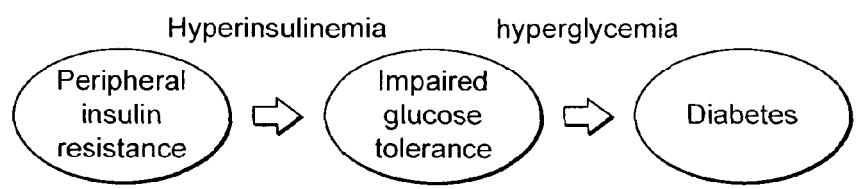

The present invention relates in general to medium chain dicarboxylic acids, their derivatives and uses thereof. In particular, the present invention relates to a composition comprising medium chain dicarboxylic acids and to the use of medium chain dicarboxylic acids and their derivatives for the preparation of products to treat or prevent metabolic disorders.

Diabetes mellitus is a metabolic condition characterized primarily by high blood glucose levels that result from the body's inability to make or use insulin. Hyperglycemia can lead to numerous clinical complications including blindness, limb amputations, heart attack or stroke. In 2007, it was estimated that 246 million of adults have diabetes, and if nothing is done to slow down the epidemic, within 25 years the number will reach more than 380 million.

The most common types of diabetes are insulin-dependent diabetes (Type-1 diabetes, T1 D) and type-2 diabetes (T2D), which is by far the most abundant type. The increase in type-2 diabetes is mainly driven by increasing obesity rates. Today, more than 1.1 billion people are estimated to be overweight, of which around 320 million are obese.

The pathophysiology of the development of T2D is complex and multifactorial. Obesity, sedentary life style and/or increased age may lead to insulin resistance and to increased circulating insulin concentrations over time. At some point a loss of control of blood glucose begins to emerge, resulting in impaired glucose tolerance (IGT) or impaired fasting glucose (IFG) and may ultimately result in T2D. Therefore IGT and IFG refer to metabolic states intermediate between normal glucose homeostasis and diabetes.

A further test, the oral glucose tolerance test (OGTT), may be performed to assess whether the patient is diabetic or has IGT. The OGTT consists of a glucose drink containing 75 g of glucose. The patient's blood sugar level is measured at one and two hours following administration of the drink.

As glucose is an essential nutrient for the human body, its circulating levels must be carefully maintained constant, in order to supply adequate amounts to peripheral tissues. The liver plays a central role in glucose homeostasis by balancing its uptake and storage via glycogenesis and its release via glycogenolysis and gluconeogenesis. An impairment of glucose homeostasis is a typical feature of T2D. Patients with T2D exhibit increased hepatic glucose production (HGP), which is identified as the main cause of fasting hyperglycaemia and is associated with a reduced plasma glucose clearance (Gastaldelli A, et al., Diabetes 2000; 49:1367-1373), and a 25-45% reduced synthesis of glycogen compared with non-diabetic subjects (Roden M, et al., Best Pract Res Clin Endocrinol Metab. 2003; 17:365-83).

Limiting blood glucose peaks after a meal in diabetic subjects also constitutes an important target of the overall glycemic control strategy.

Actual treatments for T2D comprise several classes of drugs, which can be used alone or in combination with insulin.

Biguanides work by reducing the amount of glucose produced by the liver. Obese patients with T2D are usually started on biguanides. Common side effects include abdominal discomfort, diarrhea, nausea or vomiting, loss of appetite, and metallic taste.

Alpha-glucosidase inhibitors slow the digestion of carbohydrates, delay glucose absorption, and reduce the increase in blood glucose after a meal. Common side effects include abdominal pain, diarrhea, and flatulence.

In animals and humans, medium-chain dicarboxylic acids (DA), which include adipic (C6), suberic (C8), sebacic (C10), and dodecanedioic (C12) acids, derive from co-oxidation of the corresponding fatty acids or from the β-oxidation of longer-chain dicarboxylic acids. In plants, DA are components of the natural protective polymers cutin and suberin (Mingrone G, et al., Nutr Rev. 2006; 64:449-56). DA energy density is intermediate between glucose and fatty acids.

U.S. Pat. No. 5,272,177 describes the use of sebacic acid and derivates as a suitable fuel substrate in enteral and parenteral nutrition during severe catabolic stages such as sepsis, shock, multiple trauma and burns.

Starting out from the prior art it was the object of the present invention to improve the state of the art and in particular to provide the art with a composition and a use that allows it to manage glucose levels in the blood of human or animal patients that is safe to use and does not exhibit the side effects that are common to the medications known in the art. This composition should be suitable for enteral or oral application.

The present inventors were surprised to see that this object could be achieved by the subject matter of the independent claims. The dependant claims further develop the idea of the present invention.

It was found that a composition comprising at least one medium chain dicarboxylic acid or a derivative thereof achieves the object of the present invention and can, e.g., successfully be used for the preparation of a product to treat or prevent metabolic disorders.

Consequently, one embodiment of the present invention relates to a composition comprising at least one medium chain dicarboxylic acid (DA) and/or a derivative thereof to treat or prevent metabolic disorders.

It also relates to the use of a composition comprising at least one medium chain dicarboxylic acid (DA) and/or a derivative thereof for the preparation of a product to treat or prevent metabolic disorders.

Metabolic disorders include for example peripheral insulin resistance, impaired glucose tolerance and diabetes.

Medium chain dicarboxylic acids are preferably selected from the group consisting of C4-C14 dicarboxylic acids. More preferably the medium chain dicarboxylic acids are selected from the group consisting of C6-C12 dicarboxylic acids and comprise C6, C7, C8, C9, C10, C11 and C12 dicarboxylic acids. Examples are succinic acid, glutaric acid, adipic acid, pimelic acid, suberic acid, azelaic acid, sebacic acid, phthalic acid, isophthalic acid, terephthalic acid.

Most preferred are the naturally occurring medium chain dicarboxylic acids selected from the group consisting of adipic (C6) acid, suberic (C8) acid, sebacic (C10) acid, dodecanedioic (C12) acid. The medium chain dicarboxylic acids may be used alone or in mixtures of two or more dicarboxylic acids.

The derivatives of medium chain dicarboxylic acids comprise for example all compounds which after hydration, de-esterification or acidification yield the medium chain dicarboxylic acids. The derivatives of medium chain dicarboxylic acids are preferably selected from the group consisting of salt forms of the dicarboxylic acids, preferably sodium, potassium, calcium, magnesium or amino acids salts, and esters of dicarboxylic acids, preferably glycerol esters, in particular triglycerides, or ethanol esters.

Naturally occurring medium chain dicarboxylic acids and their derivatives are in particular preferred for the purpose of the present invention. They may be isolated from naturally occurring foodstuff and are, hence, usually very well tolerated by the body. Furthermore, they may be provided in the form of extracts from foodstuff, so that no extensive purification procedure is required.

The amount of the at least one medium chain dicarboxylic acid or derivative thereof to be administered in accordance with the present invention is not particularly limited and will depend, e.g., on the weight and age of the patient to be treated, its condition, in particular health condition and the amount and kind of food consumed.

In therapeutic applications, compositions are administered in an amount sufficient to at least partially cure or arrest the symptoms of the disease and its complications. An amount adequate to accomplish this is defined as "a therapeutically effective dose".

In prophylactic applications, compositions according to the invention are administered to a patient susceptible to or otherwise at risk of a particular disease in an amount that is sufficient to at least partially reduce the risk of developing a disorder. Such an amount is defined to be "a prophylactic effective dose".

The composition of the present invention is typically used in a therapeutically effective dose and/or a prophylactic effective dose. These dosages can be determined by those of skill in the art.

Typically, the at least one medium chain dicarboxylic acid and/or derivative thereof may be present in the product and/or composition in an amount in the range of 0.5-100 g per daily dose, preferably in the range of 1 g-50 g per daily dose, for example in the range of 1 g-40 g per daily dose.

The product prepared by the use of the present invention may be a food product, a food supplement, a nutraceutical, a pet food product or a medicament, for example. It may also be a beverage or a cosmetic product.

The product, in particular if it is a food product or a beverage may also comprise a protein source, a carbohydrate source and/or a lipid source. The present inventors have found that this composition can very well be applied orally or enterally. In contrast to a parental application this has the advantage that unnecessary puncturing of the skin of the patients and corresponding risks for, e.g., infections are avoided. Furthermore, while parenteral compositions usually do not comprise a protein source, a carbohydrate source and a lipid source simultaneously, since this might lead to clotting during storage, resulting in severe health risks for the patient after injection, this is in contrast very well possible for oral and enteral application forms.

The product of the present invention may be a nutritionally complete formula.

As protein source any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

If the product includes a fat source, the fat source preferably provides 5% to 40% of the energy of the composition; for example 20% to 30% of the energy. A suitable fat profile may be obtained using a blend of canola oil, corn oil and high-oleic acid sunflower oil. Fat source may also include coconut oil or palm oil, rich in medium chain triglycerides.

A carbohydrate source may preferably provide 40% to 80% of the energy of the composition. Any suitable carbohydrate may be used, for example sucrose, lactose, glucose, fructose, corn syrup solids, maltodextrins, and mixtures thereof.

Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA and guidelines such as FSMP.

For example, the composition may contain per daily dose one or more of the following micronutrients in the ranges given: −300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin.

The product of the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The product prepared by the use of the present invention may also comprise at least one kind of food grade bacteria, in particular probiotics.

"Food grade bacteria" means bacteria that are used and generally regarded as safe for use in food. Probiotics are microorganisms which when administered in adequate amounts confer a health benefit on the host.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

Modifications of the intestinal flora are thought to be associated with obesity. These changes were demonstrated in obese mice to affect the metabolic potential of gut microbiota resulting in an increased capacity to harvest energy from the diet (Turnbaugh P J, et al., Microbial ecology: human gut microbes associated with obesity. Nature. 2006). Such modifications of the gut microbiota are proposed to contribute to the pathophysiology of obesity. Probiotics, the beneficial bacteria present in food or food supplements, are known to modify the intestinal microbiota (Fuller R & Gibson G R, Modification of the intestinal microflora using probiotics and prebiotics. Scand J. Gastroenterol. 1997).

Probiotics that are preferably used in the product of the present invention may be selected from the group consisting of *Bifidobacterium, Lactobacillus, Streptococcus* and *Saccharomyces* or mixtures thereof, in particular selected from the group consisting of *Bifidobacterium longum, Bifidobacterium lactis, Lactobacillus acidophilus, Lactobacillus rhamnosus, Lactobacillus johnsonii, Lactobacillus plantarum, Lactobacillus salivarius, Streptococcus faecium, Saccharomyces boulardii* and *Lactobacillus reuteri* or mixtures thereof, preferably selected from the group consisting of *Lactobacillus johnsonii* NCC 533 (CNCM 1-1225), *Bifidobacterium longum* NCC 490 (CNCM 1-2170), *Bifidobacterium longum* NCC 2705 (CNCM 1-2618), *Bifidobacterium lactis* Bb12, *Bifidobacterium lactis* NCC2818 (CNCM 1-3446), *Lactobacillus paracasei* NCC 2461 (CNCM 1-2116), *Lactobacillus rhamnosus* GG, *Lactobacillus rhamnosus* NCC4007 (CGMCC 1.3724) *Enterococcus faecium* SF 68 (NCIMB 10415), and mixtures thereof.

Prebiotics may also be added, for example to support the function of the probiotics or because they have a positive effect on digestion by themselves. Consequently, the product prepared by the use of the present invention may further contain at least one prebiotic.

"Prebiotic" means food substances intended to promote the growth of probiotic bacteria in the intestines. They are not broken down in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

Preferably the prebiotic may be selected from the group consisting of oligosaccharides and optionally contain galactose, mannose, soy and/or inulin; dietary fibers; or mixtures thereof.

Preferably, the product prepared by the use of the present invention is to be administered to pre-diabetic or diabetic subjects.

Insulin resistance represents an insensitivity of the peripheral tissues (e.g., muscle, liver, adipose tissue) to the effects of insulin on glucose uptake. To compensate for this, the pancreas releases much more insulin such that the cells are adequately triggered to absorb glucose. This leads to high plasma insulin levels (hyperinsulinemia). Insulin resistance in normoglycemic people is defined as a fasting plasma insulin level≥16.7 mU/l (Ascaso J F, et al., Diabetes Care. 2003: 3320-5).

Pre-diabetes is characterized by an impaired fasting glucose and an impaired glucose tolerance. At some point a loss of control of blood glucose begins to emerge, resulting in impaired glucose tolerance (IGT) or impaired fasting glucose (IFG) and may ultimately result in T2D. Therefore IGT and IFG refer to metabolic states intermediate between normal glucose homeostasis and diabetes. IFG is defined as fasting blood sugar levels of between 6.1 and 7.0 mmol/L. IGT is indicated if the blood sugar level is between 7.8 and 11.1 mmol/L two hours following administration of a glucose drink containing 75 g of glucose Diabetes is a metabolic condition characterized primarily by high blood glucose levels that result from the body's inability to make or use insulin. Fasting blood sugar levels of more than 7.8 mmol/L or blood sugar levels of more than 11.1 mmol/L indicate diabetes.

Reference is made in this respect to FIG. 1.

Type-1 diabetes (T1 D), also called insulin-dependent diabetes, is caused by an auto-immune disease reaction where the body's defense system attacks the insulin-producing cells. People with T1 D produce very little or no insulin.

Type-2 diabetes (T2D), which is the most common type (about 90% of all diabetes), is strongly associated to an excess of body fat, especially when concentrated within the abdomen.

The product prepared by the use of the present invention is considered to be in particularly effective, if it is administered during or after a meal. Of course the product prepared by the use of the present invention may be a part of the meal or may even represent a full meal. After the meal means within 1 hour, preferably within 30 minutes, even more preferred within 15 minutes after completion of the meal.

The present inventors were surprised to find that the product prepared by the use of the present invention have several beneficial effects on a body.

Subjects treated exhibited a significant decrease in postprandial glycemia. Their insulin secretion rate decreased markedly. Also the endogenous glucose production and the gluconeogenesis decreased. Simultaneously, a significant increase in postprandial glucose clearance was observed.

Consequently the product prepared by the use of the present invention may be used to treat or prevent hyperglycemia. Several disorders are linked to hyperglycemia. Consequently, these disorders may be treated or prevented by the use of the present invention as well, for example, nephropathy, retinopathy, heart and cardiovascular diseases may be prevented by the use of the present invention.

The product prepared according to the present invention may further be used to improve glucose clearance. Also, it may be used to at least partially inhibit hepatic glucose production and/or to decrease endogenous glucose production.

A further embodiment of the present invention relates to the use of the product to treat or prevent diabetes, in particular diabetes type 1 and diabetes type 2.

A further embodiment of the present invention relates to a composition, in particular a food composition, comprising at least one added medium chain dicarboxylic acid or a derivative thereof. All features described above for the use of the present invention may be applied equally to this composition of the present invention. In particular, the composition of the present invention may optionally a probiotic. Further, it may contain a prebiotic.

It is clear to those skilled in the art that they can freely combine all features described herein without departing from the scope of the invention as disclosed. In particular, all features described for the use of the present invention apply also to the composition described in the present invention and vice versa.

Further embodiments and advantages of the present invention are apparent from the following examples and figures.

FIG. 1 shows how hyperinsulinemia leads from insulin resistance to impaired glucose tolerance and how hyperglycemia leads from impaired glucose tolerance to diabetes.

Figure 2:
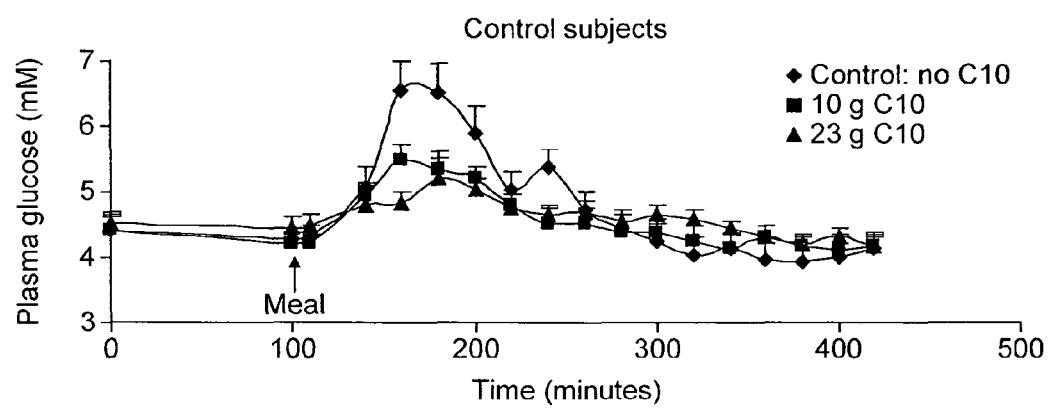
Figure 2:
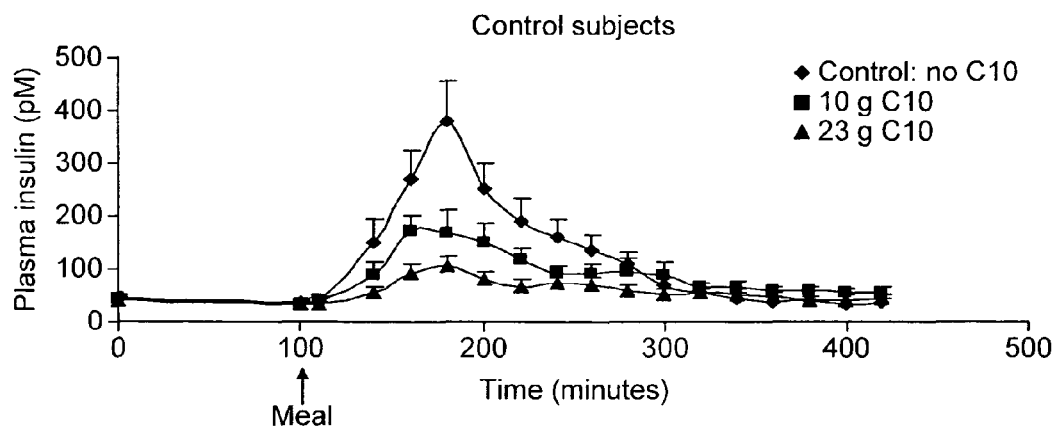

FIG. 2 shows the time course of plasma glucose and insulin in healthy people after ingestion of no C10, 50% CHO, 15% protein and 35% lipids plus water; 23 g C10, 50% CHO, 15% protein and 35% C10 DA (23 g) plus water or 10 g C10, 50% CHO, 15% protein and 35% lipids plus 10 g of C10 plus water. Ingestion of the different meals was performed at 100 min.

Figure 3:
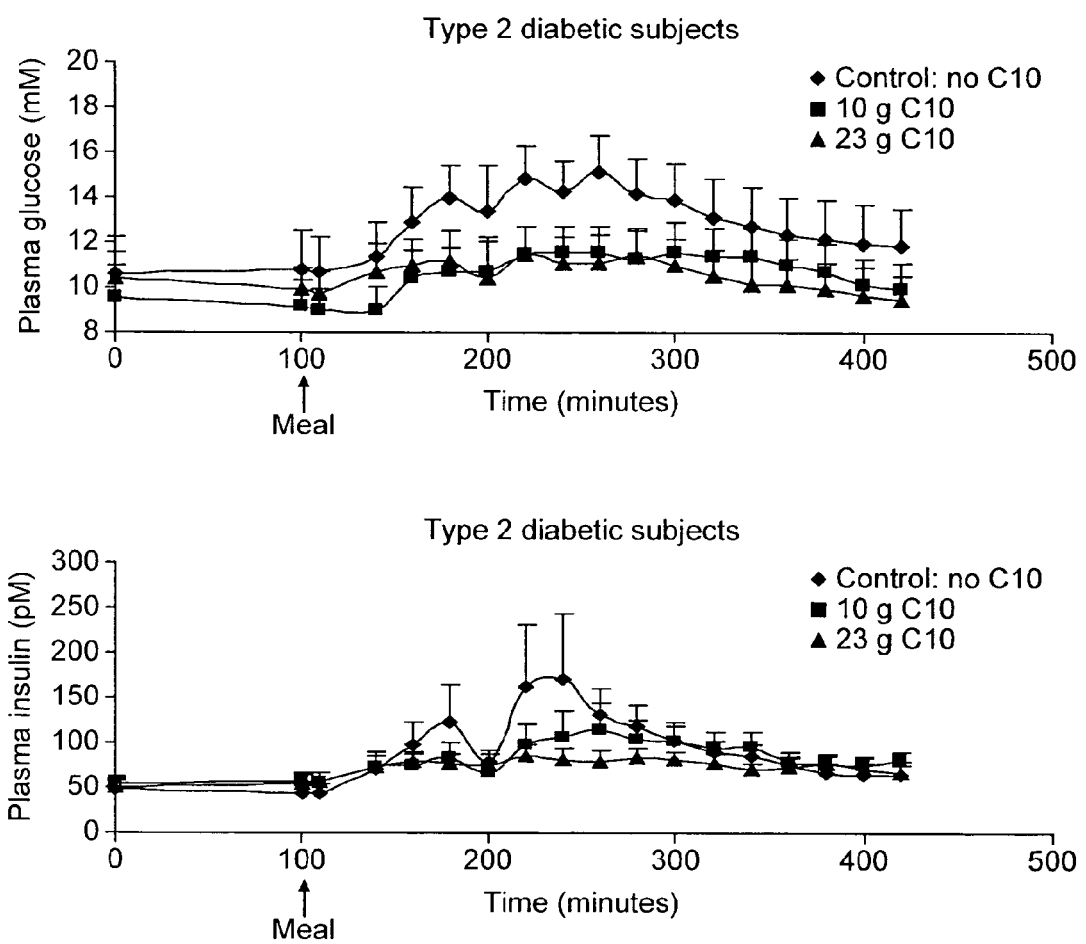

FIG. 3 shows the time course of plasma glucose and insulin in T2D patients after ingestion of no C10, 50% CHO, 15% protein and 35% lipids plus water; 23 g C10, 50% CHO, 15% protein and 35% C10 DA (23 g) plus water or 10 g C10, 50% CHO, 15% protein and 35% lipids plus 10 g of C10 plus water. Ingestion of the different meals was performed at 100 min.

Figure 4:
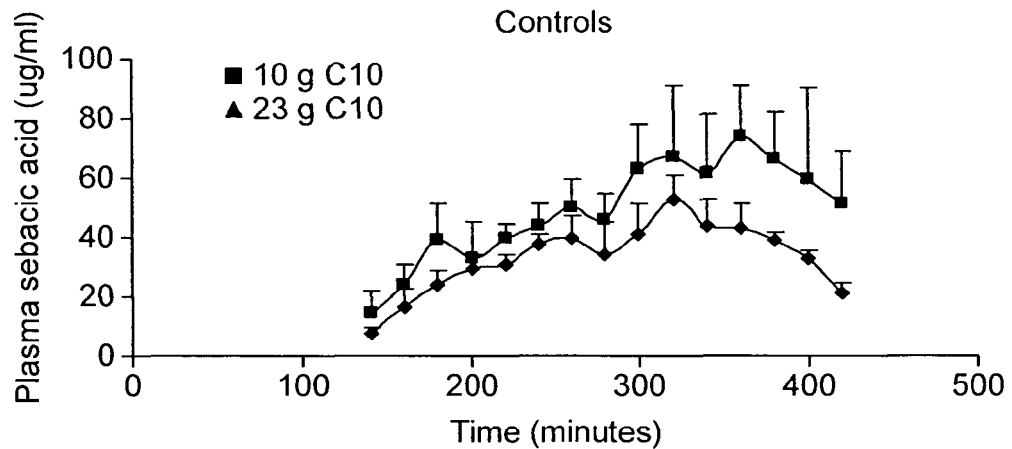

FIG. 4 reports the time course of plasma sebacate in healthy subjects.

Figure 5:
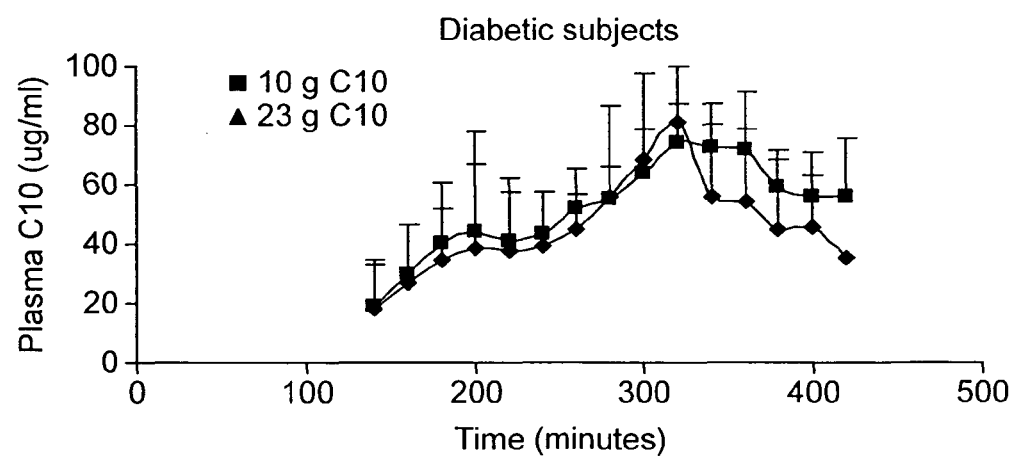

FIG. 5 reports the time course of plasma sebacate in T2D subjects.

EXAMPLES

The acute effects of oral ingestion of sebacic acid on postprandial glycemia, hepatic gluconeogenesis and glycogenolysis were tested in T2D subjects and healthy volunteers during ingestion of a mixed meal at breakfast.

Type 2 diabetic patients and healthy subjects were matched for gender distribution, age, and body mass index as reported in the following table 1:

The subjects ingested the following formula meal

No C10 group (control group): 50% CHO, 15% protein and 35% lipids plus water 23 g C10 group: 50% CHO, 15% protein and 35% C10 DA (23 g) plus water 10 g C10 group: 50% CHO, 15% protein and 35% lipids plus 10 g of C10 plus water The results of the cross-over single-blind pilot study showed in T2D subjects (n=10)

A significant decrease in postprandial:
Glycemia area under the curve (AUC) with the 10 g (−17%) and 23 g C10 DA (−16%) meal
Insulin secretion rate with the 23 g C10 DA meal (−35%)
Endogenous Glucose Production with the 10 g (−10%) and 23 g C10 DA (−9%) meal
Gluconeogenesis (%) with the 10 g (−2.1%) and 23 g C10 DA (−2.3%) meal A significant increase in postprandial:
Glucose clearance with the 10 g (+12.6%) and 23 g C10 DA (+8.2%) meal In healthy subjects (n=10), only the postprandial insulinemia AUC was significantly decreased (−38%; 23 g sebacic acid)

In T2D patients the effect of C10 was more pronounced as shown in FIG. 3 respectively for plasma glucose and plasma insulin time courses.

FIG. 4 reports the time course of plasma sebacate in healthy subjects. The peak was reached after 320 minutes from the beginning of the experiment, i.e. 200 minutes after the ingestion of the meal enriched with C10. C10 peaked later (delay of 40 minutes) after 23 g C10 ingestion.

FIG. 5 reports the time course of plasma sebacate in T2D subjects. The concentration of plasma C10 raised to values about 1.5 times higher than those reached in controls, however the peak times were maintained. Another difference was that in diabetics the two curves (10 g vs. 23 g) were overlapped up to 320 minutes, and then the concentration of C10 declined slower in the 23 g C10 fed patients compared with 10 g of C10.

Table 2 summarizes the mean values and the standard error of the means (SEM) for insulin area under the curve (AUCs), glucose AUCs and Insulin secretion Rates (ISR) after the meals. Glucose AUC was significantly lower in diabetic patients after the meal containing 10 g of C10.

The ISR was significantly reduced after the meal in which lipids were substituted with 23 g C10 in both healthy subjects and diabetic patients.

TABLE 1

| | Age | Height (cm) | Weight (kg) | BMI (kg/m$^2$) | FFM (kg) | FM (kg) |
|---|---|---|---|---|---|---|
| Healthy Subjects (4W/6M) | 47.2 ± 6.03 | 173.8 ± 7.68 | 80.8 ± 12.67 | 26.63 ± 3.03 | 62.62 ± 6.80 | 18.18 ± 8.71 |
| Type 2 Diabetic Subjects (5W/5M) | 52.1 ± 6.98 | 170.7 ± 6.53 | 81.94 ± 15.97 | 27.98 ± 4.08 | 59.86 ± 11.23 | 22.08 ± 6.80 |

TABLE 2

| 0-420 minutes | HEALTHY SUBJECTS | | | TYPE 2 DIABETIC SUBJECTS | | |
|---|---|---|---|---|---|---|
| | Mean | SEM | P | Mean | SEM | P |
| Insulin AUC No C10 (pM) | 63609.30 | 9531.96 | | 39343.20 | 7789.74 | |
| Insulin AUC 10 g C10 (pM) | 51112.80 | 8521.08 | | 33535.50 | 5527.50 | |
| Insulin AUC 23 g C10 (pM) | 39234.00 | 6780.18 | 0.022 | 29463.00 | 4315.86 | |
| Glucose AUC No C10 (mM) | 38278.08 | 1493.35 | | 52496.40 | 6474.09 | |
| Glucose AUC 10 g C10 (mM) | 37445.93 | 1354.06 | | 43655.70 | 4902.50 | 0.028 |
| Glucose AUC 23 g C10 (mM) | 38119.95 | 1034.10 | | 44185.28 | 5203.04 | 0.049 |
| Total ISR No C10 (nmol) | 105.82 | 12.62 | | 219.99 | 34.33 | |
| Total ISR 10 g C10 (nmol) | 101.15 | 16.49 | | 213.69 | 46.30 | |
| Total ISR 23 g C10 (nmol) | 93.60 | 14.00 | | 142.27 | 26.48 | 0.036 |

Table 3 reports the Endogenous Glucose Production (EGP), the total Rate of Appearance of deuterated glucose (Ra), the GlucoNeoGenesis (GNG) and the glucose clearance for both healthy subjects and type 2 diabetic patients. In type 2 diabetics EGP was significantly reduced after C10 enriched meals compared with the standard meal. GNG was higher in the diabetic patients compared with healthy subjects after the standard test meal, but it was significantly reduced after both C10 enriched meals. C10 ingestion significantly improved the glucose clearance in both healthy subjects and in diabetic patients.

TABLE 3

| | HEALTHY SUBJECTS | | | TYPE 2 DIABETIC SUBJECTS | | |
|---|---|---|---|---|---|---|
| | No C10 | 10 g C10 | 23 g C10 | No C10 | 10 g C10 | 23 g C10 |
| EGP ($\mu$mol $\cdot$ min$^{-1}$ $\cdot$ kg$_{ffm}^{-1}$) | 6.52 ± 2.45 | 6.30 ± 2.45 | 6.172 ± 0.68 | 10.97 ± 4.89 | 7.81 ± 3.27* | 7.00 ± 2.47* |
| Total Ra ($\mu$mol $\cdot$ min$^{-1}$ $\cdot$ kg$_{ffm}^{-1}$) | 20.76 ± 2.00 | 20.60 ± 2.88 | 21.20 ± 1.30 | 20.10 ± 2.70 | 19.60 ± 2.41 | 20.32 ± 2.19 |
| Gluconeogenesis (%) | 32.40 ± 5.26 | 31.28 ± 5.07 | 31.20 ± 3.63 | 42.98 ± 3.40 | 40.862 ± 3.62* | 40.72 ± 4.00[§] |
| Glucose clearance (ml $\cdot$ min$^{-1}$ $\cdot$ kg$^{-1}$) | 2.55 ± 0.30 | 2.73 ± 0.24[#] | 2.74 ± 0.26[#] | 1.58 ± 0.19 | 1.76 ± 0.13[#] | 1.71 ± 0.21[§] |

EGP, endogenous glucose production; Ra, rate of appearance; GNG, gluconeogenesis
*= P < 0.02; [#]= P < 0.01; [§]= P < 0.05

In T2D subjects, a possible explanation of the effect of sebacic acid in reducing plasma glucose concentration after a energy balanced mixed meal is that C10 DA improves tissue glucose uptake—as shown by the higher glucose clearance—and likely increases the storage of glucose in the liver, as glycogen, and decreases hepatic glucose output. Of relevance is that this effect is also observed after administration of 10 g of C10 DA, even in presence of lipids in the test meal.

A typical nutritional formula containing medium chain DA may contain 1 to 30 g DA per serving for an adult person.

The invention claimed is:

1. A food composition comprising at least one added medium chain dicarboxylic acid or medium chain dicarboxylic acid derivative that is selected from the group consisting of sebacic acid, a derivative of sebacic acid, and combinations thereof, the food composition being a beverage in which the at least one added medium chain dicarboxylic acid or medium chain dicarboxylic acid derivative is present in an amount of 1 g to 40 g per dose, the food composition further comprising a protein source providing about 15% of the energy of the food composition.

2. The food composition of claim 1, wherein the derivative of sebacic acid is selected from the group consisting of salt forms of sebacic acid and esters of sebacic acid.

3. The food composition of claim 2, wherein the salt forms of sebacic acid are selected from the group consisting of sodium, potassium, calcium, magnesium and amino acids salts of sebacic acid.

4. The food composition of claim 2, wherein the esters of sebacic acid are selected from the group consisting of glycerol esters and ethanol esters.

5. The food composition of claim 1 further comprising at least one additional dicarboxylic acid or dicarboxylic acid derivative selected from the group consisting of medium chain dicarboxylic acids, derivatives of medium chain dicarboxylic acids and mixtures thereof.

6. The food composition of claim 1 further comprising at least one probiotic.

7. The food composition of claim 6, wherein the probiotic is selected from the group consisting of Bifidobacterium, Lactobacillus, Streptococcus, Saccharomyces, and mixtures thereof.

8. The food composition of claim 1 further comprising at least one prebiotic.

9. The food composition of claim 8, wherein the prebiotic is selected from the group consisting of oligosaccharides, dietary fibers, and combinations thereof.

10. The food composition of claim 1 further comprising a carbohydrate source providing about 50% of the energy of the food composition, and a lipid source providing about 35% of the energy of the food composition.

11. A food composition comprising at least one added medium chain dicarboxylic acid or medium chain dicarboxylic acid derivative that is selected from the group consisting of sebacic acid, a derivative of sebacic acid, and combinations thereof, the at least one added medium chain dicarboxylic acid or medium chain dicarboxylic acid derivative present in the food composition in an amount of 1 g to 40 g per dose, the food composition further comprising a protein source providing about 15% of the energy of the food composition, a carbohydrate source providing about 50% of the energy of the food composition, and a lipid source providing about 35% of the energy of the food composition, and the food composition is for oral application.

* * * * *